United States Patent
Eble

(10) Patent No.: US 8,574,512 B2
(45) Date of Patent: Nov. 5, 2013

(54) LABORATORY DEVICE UNIT HAVING A LABORATORY DEVICE AND A REMOTE CONTROL

(75) Inventor: Erhard Eble, Bad Krozingen (DE)

(73) Assignee: IKA-Werke GmbH & Co. KG, Staufen (DE)

( * ) Notice: Subject to any disclaimer, the term of this patent is extended or adjusted under 35 U.S.C. 154(b) by 75 days.

(21) Appl. No.: 13/057,825

(22) PCT Filed: May 5, 2009

(86) PCT No.: PCT/EP2009/003193
§ 371 (c)(1),
(2), (4) Date: Mar. 23, 2011

(87) PCT Pub. No.: WO2010/015290
PCT Pub. Date: Feb. 11, 2010

(65) Prior Publication Data
US 2011/0165023 A1 Jul. 7, 2011

(30) Foreign Application Priority Data
Aug. 7, 2008 (DE) .......................... 10 2008 036 860

(51) Int. Cl.
*B01L 3/00* (2006.01)
*B01L 99/00* (2010.01)
*C12Q 1/68* (2006.01)
*G06F 11/30* (2006.01)
*G21C 17/00* (2006.01)

(52) U.S. Cl.
USPC .............. 422/500; 422/50; 702/122; 702/188

(58) Field of Classification Search
None
See application file for complete search history.

(56) References Cited

U.S. PATENT DOCUMENTS

| | | | |
|---|---|---|---|
| 2004/0171171 A1* | 9/2004 | Appoldt et al. ............... | 436/180 |
| 2005/0128183 A1* | 6/2005 | McGreevy .................... | 345/156 |
| 2006/0198767 A1* | 9/2006 | Fordham ....................... | 422/104 |
| 2007/0208800 A1* | 9/2007 | Frohlich et al. .............. | 709/203 |
| 2008/0182301 A1 | 7/2008 | Handique et al. | |
| 2008/0281168 A1* | 11/2008 | Gibson et al. ................. | 600/301 |

FOREIGN PATENT DOCUMENTS

| | | |
|---|---|---|
| DE | 19911397 | 10/2000 |
| DE | 202005019472 | 3/2006 |

* cited by examiner

Primary Examiner — Jill Warden
Assistant Examiner — Charles D Hammond
(74) Attorney, Agent, or Firm — Volpe and Koenig, P.C.

(57) ABSTRACT

A laboratory device unit (1) for processing or analyzing substances, mixtures or media, is provided having functional elements provided in or on a laboratory device (3) for carrying out said processing and/or analyzing. At least two remote controls (2, 6) are provided, wherein a range of functions of the functional elements can be used to a lesser extent with the one remote control (6) than with the other remote control (2).

18 Claims, 1 Drawing Sheet

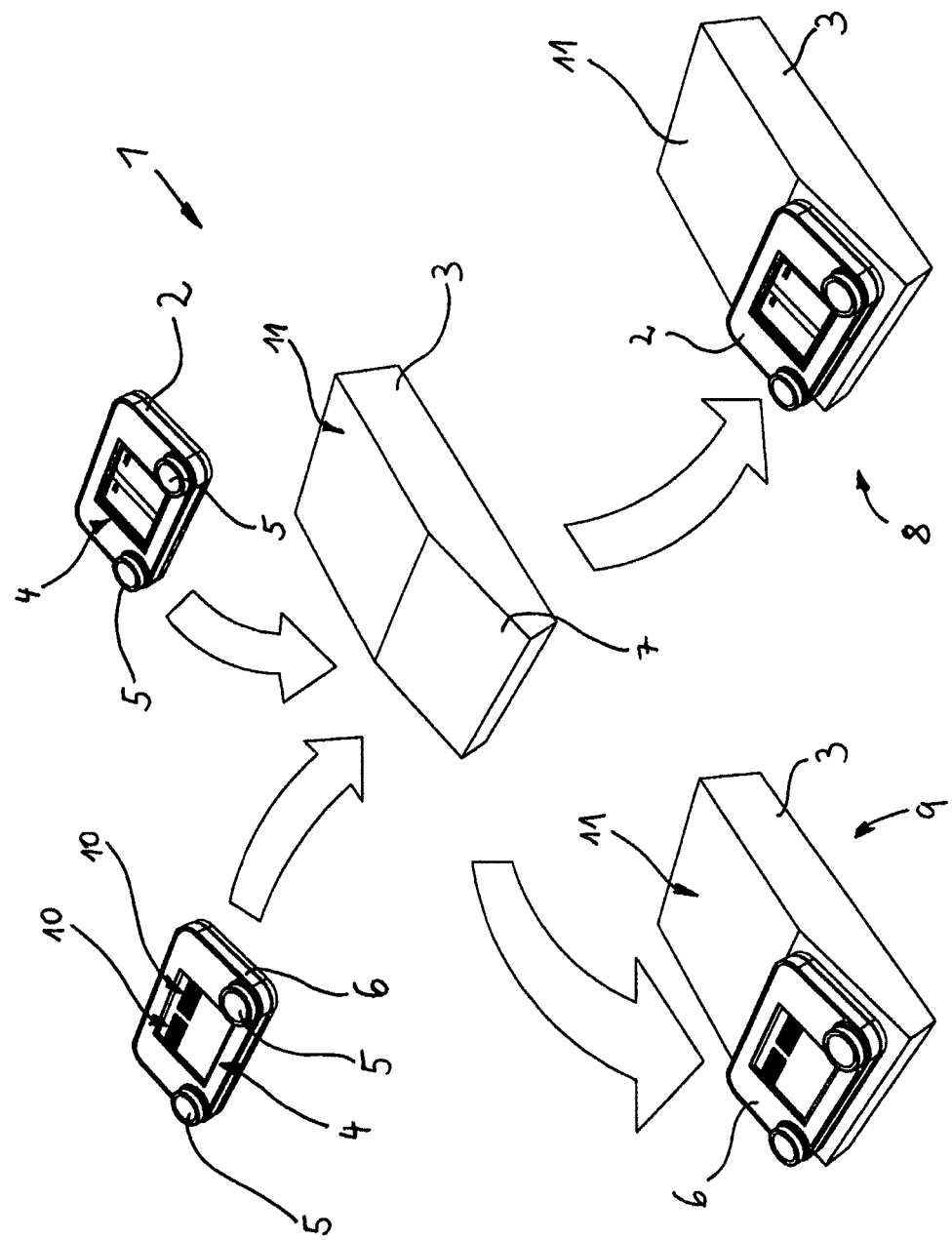

LABORATORY DEVICE UNIT HAVING A LABORATORY DEVICE AND A REMOTE CONTROL

BACKGROUND

The invention relates to a laboratory device unit having a laboratory device for processing and/or analyzing substances, mixtures, or media and having a remote control for the parameters available or adjustable within the laboratory device and/or detectable measurements.

Such laboratory device units are known, for example, from DE 199 11 397 A1.

Within the scope of further developing available laboratory devices, they frequently comprise an extensive performance spectrum and are equipped with a multitude of various functions. This leads to the consequence that the remote controls provided for their operation are also designed increasingly more expensive in order to allow using the entire scope of functions of the laboratory device.

On the other hand, frequently there is a need for cost-effective laboratory devices, which meet only simple requirements.

In order to meet these demands, manufacturers have begun to offer series of laboratory devices, in which the different variants of the laboratory devices vary by different capacities or by a differently extensive performance spectrum, for example a differently sized adjustment and/or measurement range of a parameter when using the laboratory device.

SUMMARY

The invention is based on the objective of simplifying the production of a series of laboratory devices and to reduce the production costs.

In order to attain this objective, the invention provides that in a laboratory device unit of the type mentioned at the outset the laboratory device is provided with high capacities and/or a wide performance range and/or a wide range of adjustments and/or measurements with regards to its adjustments and/or measurements and that at least two different remote controls are provided, and that one of the remote controls is designed to operate the laboratory device with high capacity and/or a wide performance spectrum and/or a wide range of adjustments and/or measurements and the other remote control is designed to operate the laboratory device to a lesser extent with regards to capacity and/or spectrum and/or range of adjustments and/or measurements. This advantageously achieves that by combining the laboratory device with one or the other remote control two different variants of a laboratory device unit are provided, in which a different scope of performance spectrum and/or capacity and/or range of adjustments and/or measurements of the laboratory device can be used. In particular, combined with the other remote control, which is the one designed to operate the laboratory device to a lesser extent with regards to capacity and/or spectrum and/or range of adjustments and/or measurements, the laboratory device acts like a laboratory device with an actually restricted scope as perceived by the user.

Therefore, the invention utilizes the surprising insight that the additional expense for a laboratory device provided with functions that cannot be used by a remote control and/or ranges of adjustments and/or measurements not accessible is rather low compared to the expense resulting from a separate production of individual variants of a series of laboratory device units. Additionally, the warehousing costs for providing the individual components for the production of the variants of the series can be reduced and the variants of the series are easily adjustable to the particular customer requirements by the design of the remote controls, while the laboratory device, requiring the majority of development work, requires no adjustment at all. Accordingly, each user perceives his/her laboratory device unit to be individually designed.

Additionally, the invention offers the advantage that a laboratory device unit with a restricted capacity and/or performance spectrum can subsequently be changed in a simple fashion into a laboratory device unit with an expanded performance spectrum by exchanging the remote controls.

Thus, for outsiders it seems that different laboratory device units are provided for the user due to the fact that the accessible performance spectrums of the laboratory device, accessible by the different remote controls, are different. Here, an appropriate design of the remote controls may also achieve that the variants of the laboratory devices of a series can theoretically be sorted in a rising order with regards to an increasingly useable performance spectrum or that various laboratory device—variants with different performance spectrums and/or different capacities are provided, which show identical intersections, however in which the performance spectrum and/or the capacity of the device unit not entirely coinciding with the one of another device unit. However, preferably one remote control shall be provided, which is designed to operate the full capacity and/or the full performance spectrum and/or the full range of adjustments and/or measurements of the laboratory device, with the second remote control being designed to operate the capacity and/or the performance spectrum and/or the range of adjustments and/or measurements to a lesser extent only. This way, using one remote control the entire multitude of performances can be accessed provided for use by the laboratory device.

In order to increase the multitude of variants of the series it may be provided that at least one additional remote control is provided, which is designed for interim values with regards to the capacity and/or the performance spectrum and/or the scope of adjustments and/or measurements of the laboratory device. Such a remote control can be designed and/or configured depending on the requirements for its application.

A particularly simple variant, sufficient for reduced requirements, results if an additional remote control is provided, by which only a portion of the adjustment parameters and/or measurements of the laboratory device can be accessed or addressed or adjusted. For example, it may be provided that the laboratory device comprises a function for heating a substance and a function for mixing said substance, particularly at various rotations, by the appropriate technical means, such as heaters or drives for an agitating function, being embodied at the laboratory device. In this case, a particularly simple variant of the laboratory device unit can be formed such that using one remote control only the heating function and/or only the agitating function can be controlled, or that only a certain adjustment range of the rotation used for agitation can be addressed, while in another remote control the expanded adjustment range and/or both functions can be controlled. For example, in another embodiment it may be provided that the laboratory device comprises a weighing function, by which the mass located in a receiver of the laboratory device can be determined, and here one of the remote controls, designed for a simple laboratory device—variant, cannot access the data of this weighing device, while another remote control is capable to read and display the measurements of this weighing device.

In order to design the remote controls, by which different performance spectrums and/or different capacities of the laboratory device may be controlled and/or accessed, it may be provided that the operating elements, for example rotary controls, knobs, touch screens, and the like, are embodied differently for the various remote controls according to the performance spectrum accessible. For this purpose, it may be provided that the remote controls differ with regards to the number of knobs, the allocation of the functions of these knobs, the adjustments possible by rotary controls, or the fields of a touch screen responding to contact, or that the operating signals received by operating elements are exchanged with the laboratory device by differently embodied processing and/or transceiver devices at the remote control.

A particularly simple series of laboratory device units, produced with little expense, results however if all remote controls are designed for the full range of the parameters existing and/or adjustable at the laboratory device and/or measurements detectable and with the remote controls, designed to recall only a portion of the performances and/or a partial range of the adjustments and/or measurements, higher-valued functions are blocked electronically and/or by way of software. This way, it is achieved in an advantageous manner that for retrofitting the functionality of a laboratory device unit it is not even necessary to exchange the remote control but the upgrade of the performance spectrum is achieved by uploading software and/or by entering a release code, i.e. that in a remote control with an electronic or software-based restriction of the range of operation said restriction can be subsequently activated.

In an advantageous embodiment of the invention it may be provided that in order to operate the laboratory device units with different performance capacities and/or different performance spectrums and/or different ranges of adjustments and/or measurements the remote controls are designed with different displays, with the remote control for the lower performance capacity and/or the smaller performance spectrum and/or the smaller range of adjustments and/or measurements comprises a simple display and the remote control for higher performances and ranges of measurements shows a more expensive display. This way, remote controls are provided sufficient for simpler applications, which can be combined with a laboratory device which per se shows the full scope of performance to form a laboratory device unit fulfilling these simple requirements.

According to one embodiment it may be provided that these displays at the remote controls are interchangeable, thus allowing an easy expansion of the performance spectrum of the laboratory device accessible by the remote control.

In order to store the remote control and prevent the loss thereof it may be provided that the remote control allocated to the laboratory device may be fixed at the laboratory device in a detachable fashion. This way, a preferred storage location is embodied for the remote control.

According to one embodiment of the invention it may be provided that the fixation for the remote control at the laboratory device comprises contacts to charge the battery provided, serving as the power supply for the remote control. This way, the operating period of the remote control can be increased, because during the periods in which the remote control is not needed it is recharged for future use.

According to one embodiment of the invention it may be provided that the fixation comprises contacts for the laboratory device at which the remote control is fixed, to address said remote control. Thus, by this addressing process advantageously an allocation is created between the remote control and the laboratory device, which avoids operating disruptions or mutual interference in case of the presence of several remote controls and/or several laboratory devices. By the common embodiment of the contacts for both addressing and recharging any allocation made can be checked and/or corrected during each recharging process.

According to one embodiment of the invention it may be provided that in these fastening positions the remote control respectively fixed at the laboratory device in a detachable fashion is coupled mechanically and/or electrically with the components of the laboratory device, creating the adjustments parameters and/or measurements. This way, even in case of radio interference and/or dysfunction of the remote control an operation of the performance capacity and/or the performance spectrum of the laboratory device is possible, by the remote control being arranged at the location provided for storage.

In order to avoid radio interferences, if a multitude of remote controls are present, it may be advantageously provided that the radio connection between the laboratory device and the remote control is deactivated in mechanically and/or electrically coupled remote controls and that the operating signals of the remote control can be transmitted via plug-in contacts. When this mechanical coupling via safety means is even fixed in a non-detachable fashion, it is achieved here that the range of functions of the laboratory device accessible by the coupled remote control cannot be subsequently expanded by using another remote control without opening this safety and thus disconnecting said coupling. This way, a laboratory device with a preferably simple scope of functions is embodied, which cannot be subsequently upgraded.

According to one embodiment of the invention it may be provided that the laboratory device comprises a weighing function as a parameter, which preferably is implemented by the feet, preferably located at the bottom and connected and/or allocated to a weighing device. Here, it is advantageous that this weighing function can be accessed and/or operated by some of the remote controls, while other remote controls cannot communicate with the weighing function so that the user of the other remote controls may perhaps not even learn of the existence of the weighing function existing in his/her laboratory device.

According to one advantageous embodiment of the invention it may be provided that the laboratory device is a magnetic agitator, which can be addressed by the remote control with a lesser scope of performance and/or smaller performance spectrum for lower rotations or for a range of lower rotations and/or lower heating temperatures than the values possible by the magnetic agitator and that at least a second remote control can address and/or access the maximum rotations and/or heating temperatures and/or a weighing function.

According to one embodiment of the invention it may be provided that control processes determined for the remote control of higher performances can be performed with adjustable parameters and/or measurements. For this purpose, the remote control comprises appropriate storage means and means for executing control programs, which are transmitted to the laboratory device as respective operating commands, even depending on measurements detected by the laboratory device.

The invention can further be used advantageously in an agitating device or a dispensing device, with one remote control being able to adjust the maximum rotation and/or temperature for a heating function and with at least one other remote control being able to adjust only reduced values in reference to the maximum values for the rotation and/or the temperatures.

BRIEF DESCRIPTION OF THE DRAWINGS

In the following, the invention is explained in greater detail using an exemplary embodiment; however, the invention is not restricted to this exemplary embodiment. Additional exemplary embodiments are apparent from combining the features of the claims with each other and with the features of the exemplary embodiment.

FIG. 1 shows an illustration of the principle to provide different remote controls for using various performance spectrums of a laboratory device.

DETAILED DESCRIPTION OF THE PREFERRED EMBODIMENTS

A laboratory device unit, in its entirety marked 1, for processing and/or analyzing substances, mixtures, or media has a remote control 2, which is embodied to influence existing or adjustable parameters and/or to detect measurements in the laboratory device unit 1.

For this purpose, the laboratory device unit 1 comprises a laboratory device 3, in which apparatuses, such as drives, heaters, weighing devices, and the like, not shown in greater detail, are arranged and embodied.

Using these devices, a performance capacity and/or a performance spectrum, particularly a range of adjustments and/or measurements is predetermined, which can be used by appropriate functional elements in or on the laboratory device 3 using the laboratory device unit 1.

In order to operate these performance spectrums, a remote control 2 is provided comprising an appropriate display 4 and operating elements 5. The remote control 2 is coupled to an appropriate transceiver in the laboratory device 3 via radio signals.

Using the operating elements 5 and the display 4, the functional elements provided in the laboratory device 3 can be adjusted and/or their signals and/or data can be detected in their full performance spectrum and/or within a range of adjustments and/or measurements defined by the remote control.

For utilizing the functional spectrum of the laboratory device unit 1 to a lesser extent, another remote control 6 is provided, which also comprises operating elements 5 and a display 4, by which the laboratory device unit 1 can be used to a lesser extent with respect to performance and/or the spectrum and/or the range of adjustment and/or measurements compared to the remote control 2, although the laboratory device 3 still provides the full performance spectrum.

The additional remote control 6 is also connected via radio signals to the transceiver in the laboratory device 3.

The laboratory device 3 offers a seemingly uniform exterior surface to the user, which allows no conclusions about the functional elements actually present in the laboratory device 3.

At the laboratory device, a receiving area 7 is embodied, at which optionally the remote control 2 or the remote control 6 can be fixed in a detachable fashion.

When the remote control 2 is combined with the laboratory device 3, a first variant 8 of the laboratory device series develops with the performance spectrum and/or scope of functions being defined by the remote control 2.

However, when the laboratory device 3 is combined with the other remote control 6, a second variant 9 of the laboratory device series develops, with its scope of functions and/or performance spectrum being defined by the other remote control 6.

The respective combination already results from making radio contact between the remote control 2, 6 and the laboratory device 3.

Plug-in contacts are embodied in the receiving area 7, not shown in greater detail, which create a plug-in connection when the remote control 2 or the other remote control 6 is fixed at the laboratory device 3 with opposite plug-in connections embodied at the remote controls 2, 6, also not shown.

This plug-in connection charges a battery provided in the remote controls 2, 6, and the radio contact between the remote control 2, 6 and the laboratory device 3 is deactivated, with the control signals between the radio control 2, 6 and the laboratory device 3 being transmitted via the plug-in contacts after this fixation of the remote control 2, 6 in the receiving area 7.

In the exemplary embodiment shown, the operating elements 5 of the remote controls 2, 6 are embodied identically, while the displays 4 are different with regards to the information that can be shown.

The display 4 of the other remote control 6 comprises only two data fields 10, at which the numeric values to be adjusted by the operating elements 5 are displayed, while the display 4 of the remote control 2 has a more complex structure, which allows displaying additional functions or even the display of control processes.

FIG. 1 only shows a schematic illustration of the laboratory device unit 1, which for reasons of clarity the illustration of the individual functional elements and the mountings and attachments being waived, which can be controlled and/or accessed by the remote controls 2, 6.

In one exemplary embodiment the laboratory device unit 1 comprises a magnetic agitator, which is arranged in the laboratory device 3. In this exemplary embodiment, this magnetic agitator can be used by placing a vessel with an agitator element onto the work platform 11 embodied at the laboratory device 3, causing the agitator element to be magnetically coupled to the magnetic agitator in the laboratory device 3.

In this exemplary embodiment, additionally a heater is provided in the laboratory device 3, by which a substance located in the vessel placed upon the work platform 11 can be heated.

Depending on the scope of functions provided, the remote controls 2, 6 can control a range of rotational of the magnetic agitator and/or a range of temperatures of the heater.

Additionally, in this exemplary embodiment, a weighing device is integrated in the feet of the laboratory device 3, which can be read by the remote control 2 in order to display the weight presently detected at the display 4 of the remote control 2.

Using the remote control 6, this weighing device cannot be used, though, because the display 4 here shows no option for displaying the weight presently determined by the weighing device.

Thus, without the remote control 2 the user can only learn of the existence of a weighing device in the laboratory device 3 by disassembling and/or destroying the laboratory device 3.

In this exemplary embodiment, additionally another remote control is available, which is not shown in FIG. 1, and which allows only to control the rotation of the magnetic agitator but not the control of the heater.

In the laboratory device unit 1 for processing or analyzing substances, mixtures, or media with functional elements to perform said processing and/or analysis, which are embodied in or at a laboratory device 3 forming the base device, at least two remote controls 2, 6 are provided, with in one remote control 6 the performance spectrum of the functional elements can be used only to a lesser extent compared to the other remote control 2.

The invention claimed is:

1. A laboratory device unit for at least one of processing or analyzing substances, mixtures, or media, comprising a laboratory device (3) having at least one of a scale, a heater, or an agitator, with at least first and second different remote controls (2, 6) configured to control existing or adjustable parameters or detectable measurements in the laboratory device (3) including for at least one of the scale, the heater, or the agitator, the laboratory device (3) the first and second different remote controls are configured to control at least one of a capacity, a performance spectrum, a range of adjustments, or a range of measurements with regards to the adjustable parameters or detectable measurements for the at least one of the scale, the heater, or the agitator, and the first remote control (2) for operating the laboratory device (3) includes controls that are configured to allow operation of the at least one of the scale, the heater, or the agitator with respect to at least one of the capacity, the performance spectrum, the range of adjustments, or the range of measurements and the second remote control (6) for operating the laboratory device (3) includes controls that are configured to allow operation of the at least one of the scale, the heater, or the agitator with a reduction to at least one of the capacity, the spectrum, the range of adjustments, or the range of measurements.

2. A laboratory device unit according to claim 1, wherein the first remote control (2) is configured to operate at at least one of a full capacity, a full performance spectrum, a full range of adjustments, or a full range of measurements of the laboratory device (3).

3. A laboratory device unit according to claim 1, wherein at least one additional remote control (6) is provided, which is configures to operate at interim values with regards to at least one of the capacity, the performance spectrum, the range of adjustments, or the range of measurements of the laboratory device (3).

4. A laboratory device unit according to claim 1, wherein an additional remote control (6) is provided, by which only a portion of the parameters or measurements of the laboratory device (3) are accessed or addressed or controlled.

5. A laboratory device according to claim 1, wherein all of the remote controls (2, 6) are configures to operate the full range of the existing or adjustable parameters or detectable measurements and the second remote control (2, 6) provided for recalling only a portion of the capacities or the range of the adjustment or the range of measurements, includes electronic or software blocking of higher valued functions.

6. A laboratory device unit according to claim 5, wherein the second remote control (2, 6) with higher valued functions blocked by electronics or software includes a feature for release of the electronic or software blocking.

7. The laboratory device unit according to claim 1, wherein the remote controls configured to operate the laboratory device (3) having different capacities or different performance spectrums or different ranges of adjustments or different ranges of measurements comprise different displays (4), with the second remote control (2, 6) for the lower capacity or the lower performance spectrum or the smaller ranges of adjustments or the smaller ranges of measurements comprising a simple display (4) and the first remote control (2, 6) for the higher performances and measurement ranges comprising a more expensive display (4).

8. A laboratory device unit according to claim 7, wherein the displays on the remote controls (2, 6) are interchangeable.

9. A laboratory device unit according to claim 1, wherein the remote control (2, 6) allocated to the laboratory device (3) are fixed thereon in a detachable fashion.

10. A laboratory device unit according to claim 9, wherein a fixation for the remote control (2, 6) to the laboratory device (3) includes contacts to charge a battery serving as a power supply for the remote control (2, 6).

11. A laboratory device unit according to claim 10, wherein the fixation comprises contacts for the laboratory device (3) at which the remote control (2, 6) is fixed to address the remote control (2, 6).

12. A laboratory device unit according to claim 9, wherein in a holding position, the remote control (2, 6) respectively fixed to the laboratory device (3) in a detachable fashion is at least one of mechanically or electrically coupled to components of the laboratory device (3) creating the parameters or the measurements.

13. A laboratory device unit according to claim 12, wherein a radio connection between the laboratory device (3) and the remote control (2, 6) is deactivated for the mechanically or electrically coupled remote controls (2, 6) and operating signals are transmitted via plug-in connections.

14. A laboratory device unit according to claim 1, wherein the laboratory device comprises a weighing function as a parameter, that is implemented by support feet located at a bottom and connected or allocated to a weighing device.

15. A laboratory device unit according to claim 1, wherein the laboratory device is a magnetic agitator (3), which is controllable with the second remote control (6) of lower capacity or lower performance spectrum at a lower rotation or within a range of lower rotations or lower heating temperature than values possible for the magnetic agitator (3) and that maximum rotations or heating temperatures or a weighing function are controllable or accessible by at least the first remote control (2).

16. A laboratory device unit according to claim 1, wherein certain control processes with changing parameters or measurements are performed using the remote control (2) for higher capacities.

17. A laboratory device unit according to claim 1, wherein the laboratory device is an agitator or a dispersing device (3) and a maximum rotation or temperature is adjustable with the first remote control (2) and with at least the second remote control (6) only values are adjustable for the rotation or temperatures that are reduced in reference to maximum values.

18. A laboratory device unit for at least one of processing or analyzing substances, mixtures, or media, comprising a laboratory device (3), with a remote control (2, 6) configured to control existing or adjustable parameters or detectable measurements in the laboratory device (3) including for at least one of a scale, a heater, or an agitator, the laboratory device (3) is provided with at least one of a capacity, a performance spectrum, a range of adjustments, or a range of measurements with regards to the adjustable parameters or detectable measurements for the at least one of the scale, the heater, or the agitator, and the remote control (2) for operating the laboratory device (3) is configured to operate a full range of the existing or adjustable parameters or detectable measurements in the laboratory device, and the remote control includes electronic or software configured to block certain functions to allow a limited range of operation of the laboratory device with respect to the adjustable parameters or detectable measurements.

* * * * *